(12) United States Patent
Ivanova et al.

(10) Patent No.: US 11,219,603 B2
(45) Date of Patent: Jan. 11, 2022

(54) STABLE DOSAGE FORM OF ETIDRONATE-CYTARABINE CONJUGATE, AND USE THEREOF

(71) Applicant: MAXWELL BIOTECH GROUP LTD., Moscow (RU)

(72) Inventors: Ekaterina Alekseevna Ivanova, Moscow (RU); Alexander Karpeisky, Lafayette, CO (US); Shawn P. Zinnen, Denver, CO (US); Lisa Lynn Caralli, Del Mar, CA (US); Rina Diana Fong, San Diego, CA (US)

(73) Assignee: MAXWELL BIOTECH GROUP LTD., Moscow (RU)

( * ) Notice: Subject to any disclaimer, the term of this patent is extended or adjusted under 35 U.S.C. 154(b) by 0 days.

(21) Appl. No.: 15/780,384

(22) PCT Filed: Nov. 28, 2016

(86) PCT No.: PCT/RU2016/050076
§ 371 (c)(1),
(2) Date: May 31, 2018

(87) PCT Pub. No.: WO2017/095274
PCT Pub. Date: Jun. 8, 2017

(65) Prior Publication Data
US 2019/0038559 A1 Feb. 7, 2019

(30) Foreign Application Priority Data
Dec. 1, 2015 (RU) .......................... RU2015151450

(51) Int. Cl.
*A61K 9/19* (2006.01)
*A61K 31/663* (2006.01)
(Continued)

(52) U.S. Cl.
CPC .............. *A61K 9/19* (2013.01); *A61K 31/663* (2013.01); *A61K 31/7068* (2013.01); *A61K 47/02* (2013.01); *A61P 35/04* (2018.01)

(58) Field of Classification Search
CPC ........ A61K 31/663; A61K 9/19; A61K 47/02; A61K 31/7068; A61P 35/04
See application file for complete search history.

(56) References Cited

U.S. PATENT DOCUMENTS 4,810,486 A 3/1989 Kelly et al.
5,428,181 A 6/1995 Sugioka et al.
(Continued)

FOREIGN PATENT DOCUMENTS

CA 2 376 258 12/2000
RU 2 068 262 10/1996
(Continued)

OTHER PUBLICATIONS

HBSS (Hank's Balanced Salt Solution) recipe and preparation: retrieved from internet: https://www.aatbio.com/resources/buffer-preparations-and-recipes/hbss-hanks-balanced-salt-solution. Retrieved on Feb. 25, 2019.*

(Continued)

*Primary Examiner* — Hong Yu
(74) *Attorney, Agent, or Firm* — Nixon & Vanderhye P.C.

(57) ABSTRACT

The invention relates to the field of medicine and pharmaceuticals and particularly to a novel dosage form of an antitumor preparation, which ensures the hydrolytic and physical stability of said preparation, as well as to a method for producing a dosage form of this type. The stable dosage form is a lyophilizate comprising an etidronate-cytarabine conjugate or a pharmaceutically acceptable salt thereof, and a stabilizer, which is a divalent metal salt, in a molar ratio of stabilizer to conjugate of 1:1 to 20:1. A dosage form of this (Continued)

a)

b)

type ensures the hydrolytic and physical stability of the conjugate during long-term storage, and the stability of solutions of the conjugate for parenteral administration during clinical use.

18 Claims, 3 Drawing Sheets

(51) Int. Cl.
   *A61K 31/7068* (2006.01)
   *A61K 47/02* (2006.01)
   *A61P 35/04* (2006.01)

(56) References Cited

U.S. PATENT DOCUMENTS

| | | | |
|---|---|---|---|
| 6,383,999 | B1 | 5/2002 | Coyle et al. |
| 6,896,871 | B2 | 5/2005 | Karpeisky et al. |
| 9,216,204 | B2 | 12/2015 | Karpeisky et al. |
| 2001/0041689 | A1 | 11/2001 | Padioukova et al. |
| 2003/0175313 | A1 | 9/2003 | Garrec et al. |
| 2010/0160208 | A1 | 6/2010 | Schlingensiepen et al. |
| 2013/0184447 | A1 | 7/2013 | Piccariello |
| 2014/0051625 | A1* | 2/2014 | Karpeisky ............ A61K 31/675 514/2.3 |
| 2014/0234210 | A1* | 8/2014 | Lin ........................ A61K 49/00 424/1.21 |
| 2015/0165027 | A1 | 7/2015 | Ikeda et al. |

FOREIGN PATENT DOCUMENTS

| | | |
|---|---|---|
| RU | 2 116 069 | 7/1998 |
| RU | 2 238 736 | 10/2004 |
| RU | 2 303 997 | 8/2007 |
| RU | 2 433 822 | 11/2011 |
| RU | 2 525 392 | 8/2014 |
| WO | WO 2009/152440 A1 * | 12/2009 |
| WO | WO 2012/008845 | 1/2012 |

OTHER PUBLICATIONS

Hanks' balanced salts (HBSS): https://www.itwreagents.com/download_file/product_infos/A3140/en/A3140_en.pdf. retrieved on Jul. 8, 2019.*

Magnesium Sulfate In 5% Dextrose Injection, USP: http://wgcriticalcare.com/wp-content/uploads/2016/09/WGCC_Mag_Sulf_Dex_PI_Rev_Nov_2015.pdf. Retrieved on Jul. 8, 2019.*

Reinholz et al., "A Promising Approach for Treatment of Tumor-Induced Bone Diseases: Utilizing Bisphosphonate Derivatives of Nucleoside Antimetabolites" *Bone*, Jul. 2010; 47(1): 12-22, doi:10.1016/j.bone.2010.03.006.

Ora et al., "Bisphosphonate Derivatives of Nucleoside Antimetabolites: Hydrolytic Stability and Hydroxyapatite Adsorption of 5'-β,γ-Methylene and 5'-β,γ-(1-Hydroxyethylidene) Triphosphates of 5'-Fluorouridine and ara-Cytidine" *J. Org. Chem.*, 2008, 73, 4123-4130.

Zinnen et al., "Phase 1 study of the bone-targeting cytotoxic conjugate, etidronate-cytosine arabinoside (MBC-11), in cancer patients with bone metastases" *J Clin. Oncol*, 2017, 35:15_suppl, 2589.

Schenkein et al., "Accelerated Bone Formation Causing Profound Hypocalcemia in Acute Leukemia" *Annals of International Medicine*, 1986;105: 375-378.

Farrell et al., "Bisphosphonate conjugation for bone specific drug targeting" *Bone Reports*, 9 (2018) 47-60.

International Search Report issued in PCT/RU2016/050076 dated Mar. 6, 2017.

International Preliminary Report on Patentability issued in PCT/RU2016/050076 dated Jun. 6, 2018.

A Trial of MBC-11 in Patients With CIBD, Feb. 3, 2016, https://www.bioportfolio.com/resources/trial/152422/A-Trial-of-MBC-11-in-Patients-With-CIBD.html.

Meier, "Nucleoside diphosphate and triphosphate prodrugs—An unsolvable task?" Antiviral Chemistry and Chemotherapy, vol. 25, No. 3: 69-82 (2017).

Office Action issued in U.S. Appl. No. 16/318,852 dated Mar. 13, 2020.

Gega et al., "Successful Chemotherapeutic Modality of Doxorubicin Plus Dacarbazine for the Treatment of Desmoid Tumors in Association With Familial Adenomatous Polyposis" *Journal of Clinical Oncology*, vol. 24, No. 1: 102-105 (2006).

Williams, "Magnesium Ion Catalyzed ATP Hydrolysis" *J. Am. Chem. Soc.*, vol. 122, No. 48: 12023-12024 (2000).

Miller et al., The Hydrolysis of γ-Diphenylpropul Di- and Triphosphates, Journal of the American Chemical Society, 88:7, pp. 1507-1511 (1966).

Tetas et al., The Effect of Bivalent Metal Ions on the Hydrolysis of Adenosine Di- and Triphosphate, Biochemistry, Vo. 2, No. 2, pp. 350-357 (1962).

* cited by examiner

STABLE DOSAGE FORM OF ETIDRONATE-CYTARABINE CONJUGATE, AND USE THEREOF

This application is the U.S. national phase of International Application No. PCT/RU2016/050076 filed Nov. 28, 2016 which designated the U.S. and claims priority to Russian Patent Application No. 2015151450 filed Dec. 1, 2015, the entire contents of each of which are hereby incorporated by reference.

FIELD OF INVENTION

The invention relates to the field of medicine and pharmaceuticals and particularly to a novel dosage form of an antitumor preparation, which ensures the hydrolytic and physical stability of said preparation, as well as to a method for producing a dosage form of this type.

BACKGROUND OF THE INVENTION

Bisphosphonates are synthetic analogues of pyrophosphates and are characterized by a phosphorus-carbon-phosphorus bond (in comparison with a phosphorus-oxygen-phosphorus bond in pyrophosphate) present in the molecule backbone structure, which provides for their hydrolytic stability, as well for the suitability for the treatment of degenerative bone diseases. The chemical and biological properties of bisphosphonates vary depending on the various substituents of the carbon atom in the phosphorus-carbon-phosphorus bond.

Bisphosphonates feature a high chemical affinity for hydroxyapatite, so that, by binding to the bone surface, they inhibit the activity of osteoclasts—cells, whose function is bone resorption. Bisphosphonates can also have an effect on osteoblasts, which play an important role in bone formation. Thus, bisphosphonates are used in clinical practice to inhibit bone resorption in such diseases as Paget's disease, osteoporosis, bone metastases, as well as hypercalcemia, in both malignant and benign conditions. Bisphosphonates are also used to regulate the side effects of antitumor therapy by altering the bone surface and its microenvironment, by inhibiting specific enzyme chains, and by stimulating apoptosis in osteoclasts and cancer cells.

The currently used in treatment bisphosphonates include alendronate, clodronate, etidronate, pamidronate, tiludronate, ibandronate, zoledronate, olpadronate, risedronate and neridronate. In addition, complexes of technetium-99 m with bisphosphonic acid compounds are used to obtain high resolution images for bone scanning (U.S. Pat. No. 4,810,486). Bisphosphonate derivatives were used as therapeutic agents in the treatment of such bone diseases as osteoporosis, rheumatoid arthritis and osteoarthritis (U.S. Pat. No. 5,428,181).

Monthly performed intravenous injections of bisphosphonates, in addition to chemo-, hormono- and radiotherapy, have become a modern international standard for the treatment of patients with bone metastases of malignant tumors, as well as for the treatment of patients with multiple myeloma.

The delivery of a chemotherapeutic agent (at the concentration necessary for destruction of the tumor) to the bone tissue, is a recurring problem in the treatment of patients with bone metastases. The search for a combination with maximum strength and acceptable toxicity is a challenge for researchers in the development of antitumor drugs.

A conjugate of two molecules (MBC-11) was developed and synthesized chemically as a solution of the problem: etidronate—bisphosphonate aimed at the prevention of bone destruction, and cytarabine—a cytotoxic agent destroying cancer cells (Monica M. Reinholz et. al., A promising approach for treatment of tumor-induced bone diseases: utilizing bisphosphonate derivatives of nucleoside antimetabolite//. Bone., 2010, 47(1), 12-22).

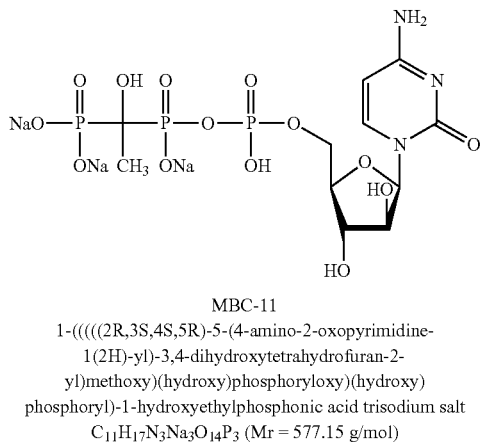

MBC-11
1-(((((2R,3S,4S,5R)-5-(4-amino-2-oxopyrimidine-1(2H)-yl)-3,4-dihydroxytetrahydrofuran-2-yl)methoxy)(hydroxy)phosphoryloxy)(hydroxy)phosphoryl)-1-hydroxyethylphosphonic acid trisodium salt
$C_{11}H_{17}N_3Na_3O_{14}P_3$ (Mr = 577.15 g/mol)

The mode of action of the drug substance represented by the etidronate-cytarabine conjugate is based on the ability of the bisphosphonate moiety to direct the conjugate to the sites of bone destruction. The conjugate stability in the blood flow after intravenous administration is such that it provides the time necessary to release the antitumor agent mainly into the bones. When the drug substance finds its way to the site of bone destruction, it is hydrolysed with the formation of cytarabine and etidronate, each of which affects the invaded tissues: cytarabine inhibits the tumor growth, and the bisphosphonate suppresses the bone resorption caused by the effect of cancer cells concentrated on the bone surface.

However, the clinical use of the etidronate-cytarabine conjugate is impossible as yet, due to the fact that the conjugate is unstable both in acid medium (which, combined with low bioavailability, complicates its oral administration), and in aqueous solutions (which complicates its parenteral administration).

SUMMARY OF THE INVENTION

An object of the present invention is to provide a dosage form of an etidronate-cytarabine conjugate or a pharmaceutically acceptable salt thereof suitable for parenteral administration during clinical use.

The technical result of the present invention is to produce a stable dosage form of an etidronate-cytarabine conjugate or a pharmaceutically acceptable salt thereof for parenteral administration, which is highly effective in the treatment of bone lesions caused by malignant neoplasms and ensures hydrolytic and physical stability of conjugate solutions for parenteral administration.

The said technical result is achieved by providing a stable dosage form of an etidronate-cytarabine conjugate or a pharmaceutically acceptable salt thereof, which is a lyophilizate for a solution for parenteral administration comprising an etidronate-cytarabine conjugate, or a pharmaceutically acceptable salt thereof, and a stabilizer, which is a divalent metal salt, with a molar ratio of stabilizer to etidronate-cytarabine conjugate, or pharmaceutically acceptable salt thereof, of 1:1 to 20:1 in the lyophilizate.

In some embodiments, the pharmaceutically acceptable salt of the etidronate-cytarabine conjugate is represented by the trisodium salt of the etidronate-cytarabine conjugate.

In some embodiments, magnesium or calcium salts are used as the divalent metal salt.

In some embodiments, calcium chloride or magnesium chloride is used as the divalent metal salt.

In some embodiments, the molar ratio of stabilizer to etidronate-cytarabine conjugate, or a pharmaceutically acceptable salt thereof, is from 1:1 to 12:1.

In some embodiments, the molar ratio of stabilizer to etidronate-cytarabine conjugate, or a pharmaceutically acceptable salt thereof, is from 1:1 to 2:1.

In some embodiments, the molar ratio of stabilizer to etidronate-cytarabine conjugate, or a pharmaceutically acceptable salt thereof, is 2:1.

The achievement of the said technical result is also possible, if the method for the production of the above said stable dosage form, comprising the following steps, is used:
- prepare an aqueous solution containing an etidronate-cytarabine conjugate, or a pharmaceutically acceptable salt thereof, and a stabilizer which is a divalent metal salt, with the selected molar ratio of stabilizer to conjugate from 1:1 to 20:1;
- perform sterile filtration of the solution produced;
- dispense the solution produced to containers for lyophilization;
- perform lyophilization.

In some alternative methods, the molar ratio of stabilizer to conjugate is from 1:1 to 12:1.

In some alternative methods, the molar ratio of stabilizer to conjugate is from 1:1 to 2:1.

In some embodiments, the molar ratio of stabilizer to conjugate is 2:1.

In certain embodiments, the concentration of the etidronate-cytarabine conjugate, or a pharmaceutically acceptable salt thereof, in the solution for lyophilization is ≤25 mg/mL.

In particular embodiments, 20 mL vials are used as containers.

In some embodiments, the sterile filtration of the solution produced is performed through a 0.2 μm sterile filter.

The present invention also relates to a reconstituted solution for parenteral administration obtained by dissolving the above said stable dosage form in a pharmaceutically acceptable solvent suitable for parenteral administration.

In some embodiments, the concentration of the stable dosage form in the reconstituted lyophilizate solution is ≤0 mg/mL.

In yet other embodiments, the pharmaceutically acceptable solvent is sterile water for injection or dextrose 5% in water (D5W).

The invention also relates to the use of the above said formulation of the etidronate-cytarabin conjugate, or a pharmaceutically acceptable salt thereof, for the treatment of primary bone cancer or bone lesion caused by a malignant neoplasm.

In particular embodiments, bone lesion is a multiple myeloma, bone metastases caused by breast, prostate or thyroid cancer, or metastatic lesions of other tissues and organs.

In some cases, the primary bone cancer is represented by osteosarcoma, Ewing's sarcoma, chondrosarcoma, fibrosarcoma.

DEFINITIONS (TERMS)

Figure 1:
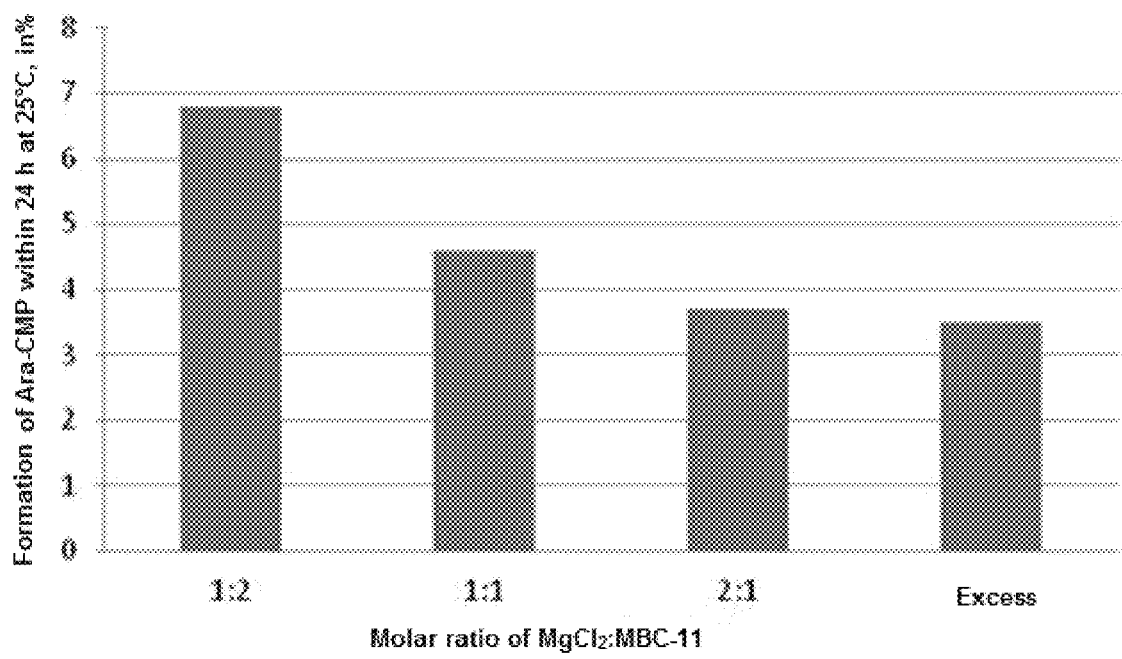
FIG. 1. The effect of magnesium chloride on the formation of arabinosylcytosine monophosphate (Ara-CMP) in an aqueous solution of the trisodium salt of the etidronate-cytarabine conjugate (MBC-11). The term "Excess" refers to the ratio of MgCl2:MBC-11 of 12:1.
Figure 2:
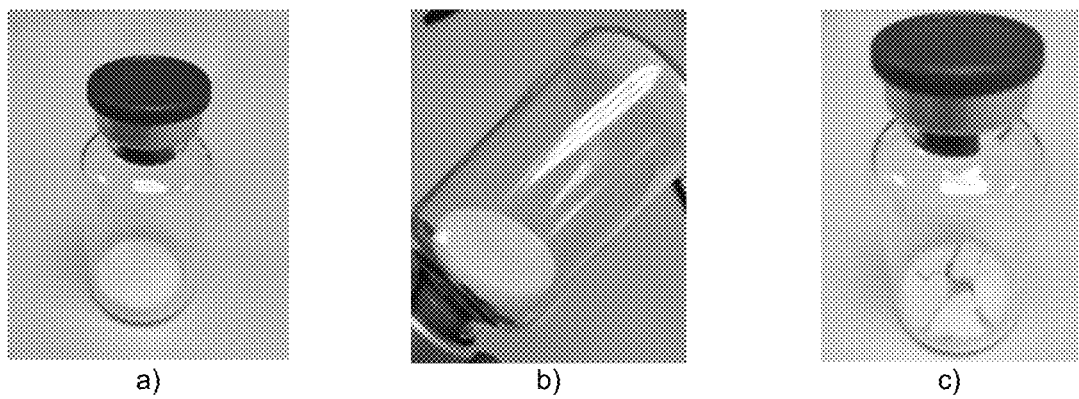
Figure 3:
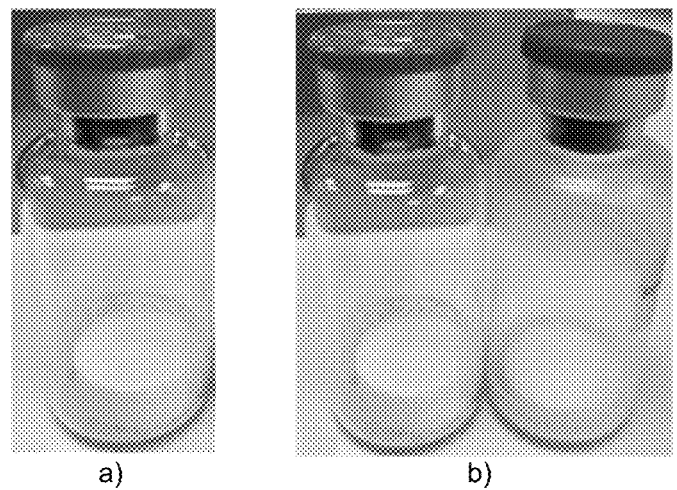
FIG. 3. 20 mL vials with lyophilized dosage form: a) MBC-11 concentration is 20 mg/mL, the vial is filled to 5 mL; b) MBC-11 concentration is 20 mg/mL, the vial is filled to 5 mL (left), in comparison with the MBC-11 concentration of 50 mg/mL, the vial is filled to 2 mL (right).
Figure 4:
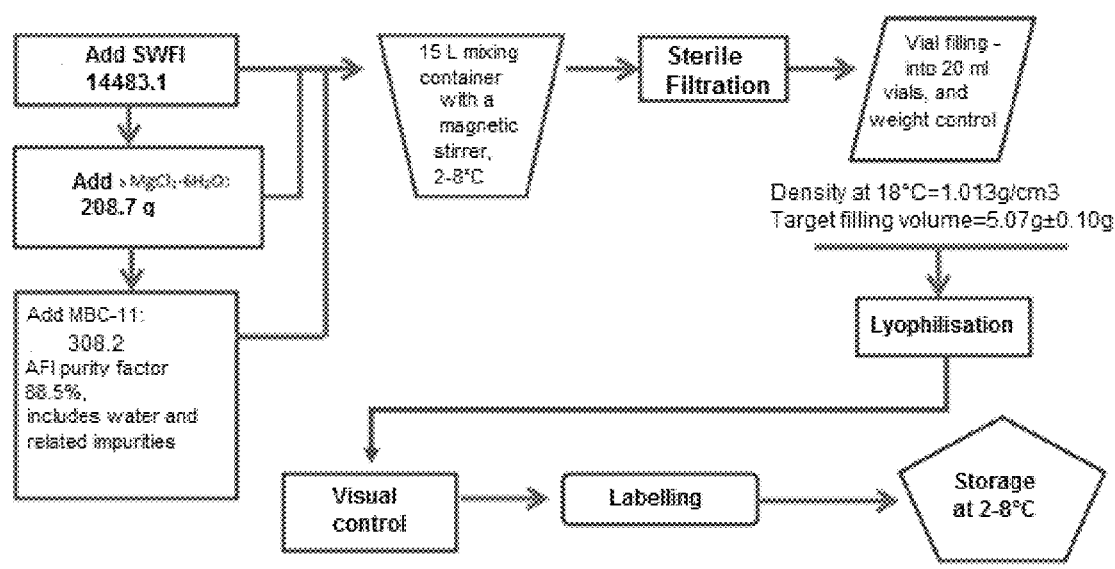
FIG. 4. The diagram of producing a batch of the finished medicinal product of the present invention in the amount of 15 liters (~3000 vials with the filling volume of 5.0±0.1 mL).

As used herein, the term "pharmaceutically acceptable salt" refers to those salts, which, within the scope of the medical assessment performed, are suitable to contact with human and animal tissues without excessive toxicity, irritation, allergic reaction, etc., and meet a reasonable risks and benefits ratio. Non-limiting examples of pharmaceutically acceptable salts of the invention include trisodium, disodium, monosodium, trilithium, dilithium, monolithium salts, etc.

As used herein, the term "divalent metal salts" refers to inorganic and organic calcium and magnesium salts. Examples of acceptable and non-toxic acid salts include salts formed with inorganic acids, such as hydrochloric, hydrobromic or perchloric acid, or with organic acids such as acetic, citric or maleic acids.

As used herein, the term "pharmaceutically acceptable solvent" refers to solvents that are not toxic or harmful to the patient when used in the compositions of this invention, including parenteral administration using methods described herein. It is understood that the solvent should be able to dissolve the appropriate amount of the dosage form of the invention, preferably at moderate stirring at room temperature. Examples of pharmaceutically acceptable solvents within the scope of the present invention may include sterile water for injection, dextrose 5% in water (D5W), normal saline solution, in particular isotonic saline solution, and others.

As used herein, the term "parenteral administration" means intravenous, intraarterial, intramuscular, intraosseous, intraarticular, subcutaneous, or intrathecal administration. The administration can be performed by injection of a small volume (up to 100 mL), or by infusion.

The term "therapeutically effective amount (therapeutic dose)" means the amount of a drug substance (or medicinal product) administered or rendered to a patient, and the administration of which is most likely to cause the patient to develop the expected therapeutic effect. The exact amount required may vary from subject to subject depending on the patient's age, body weight and performance status, disease severity, mode of drug administration, combination treatment with other drugs, etc. In particular, doses of 0.001 to 50 mg/kg are therapeutically effective for the etidronate-cytarabine conjugate, or a pharmaceutically acceptable salt thereof, more preferably—from 0.001 to 25 mg/kg, even more preferably—from 1 to 25 mg/kg. Herewith, the term "patient" means a human or an animal, whose disease needs to be treated or prevented by means of the conjugate. The etidronate-cytarabine conjugate, or a pharmaceutically acceptable salt thereof, is administered to a patient needed to treat at a dose sufficient to achieve a therapeutic effect. During the treatment, the medicinal product can be administered either once or several times a day, a week (or at any other time interval). In addition, the combination can be injected into the patient's body daily within a certain period of days (for example, per 2-10 days), followed by the drug free period (for example, 1-30 days).

DETAILED SPECIFICATION

For the invention of the pharmaceutical compositions suitable for parenteral administration, the aqueous solution of the finished dosage form of the medicinal product must have a stability that provides a time sufficient for its clinical preparation, short-term storage and use. In addition, the finished form itself must be sufficiently stable for long-term storage.

It has been established the stability of pharmaceutical compositions in long-term storage can be achieved by means of lyophilization. The studies performed have shown that the administration of divalent metal salts slightly increases the hydrolytic stability of aqueous solutions of the etidronate-cytarabine conjugate, or pharmaceutically acceptable salts thereof. However, none of the above said approaches provides for a stable dosage form of the etidronate-cytarabine conjugate, or a pharmaceutically acceptable salt thereof, for parenteral administration. The combined use of these two approaches is, then, complicated by the fact that divalent cations tend to reduce the glass transition temperature, which exacerbates the lyophilization process. In addition, divalent cations cause physical instability (contribute to sedimentation) of reconstituted lyophilizate solutions.

As a result of the studies performed, it was unexpectedly found that if divalent metal salts are used in solutions of the etidronate-cytarabine conjugate, or a pharmaceutically acceptable salt thereof, the effect of divalent cations on the production of a stable dosage form depends on the ratio of divalent metal salts and conjugate in the solution for lyophilization, that the favorable ratio of stabilizer to conjugate is at least 1:1, more optimal is the ratio from 1:1 to 20:1, even more optimal—from 1:1 to 12:1, and even more optimal—from 1:1 to 2:1. With this ratio of components, not only the hydrolytic stability of the conjugate is ensured, but also the effective completion of all stages of its lyophilization process. The resulting lyophilizates remain stable for a long time (up to several years) and have optimum solubility, and the solutions resulted from them are physically and hydrolytically stable for several hours, which makes it possible to use them for parenteral administration during clinical use of same.

The possibility of an objective demonstration of the technical result, when the invention is used, is confirmed by reliable data given in the examples containing experimental data obtained in the course of research on the methods adopted in this field. The nature of the invention is illustrated by the figures.

It should be understood, that these and all of the examples provided in the application materials are not intended to be limiting and are given only to illustrate the present invention.

Investigation of the Influence of Divalent Magnesium and Calcium Cations on the Hydrolytic Stability of the Etidronate-Cytarabine Conjugate The ability of divalent metal ($MgCl_2$ and $CaCl_2$) salts to inhibit the hydrolysis of the etidronate-cytarabine conjugate was studied.

The present invention displays specific conjugate concentrations and ratios of divalent metal salts and conjugate, which have all at once allowed to stabilize the drug in an aqueous solution and achieve optimum lyophilization conditions.

Studies were performed, where magnesium chloride was investigated as a stabilizer against hydrolytic decomposition. $MgCl_2$ was added to solutions of MBC-11 conjugate in water, tartrate buffer (50 mmol/L, pH 5) and succinate buffer (50 mmol/L, pH 5). The following molar ratios of $MgCl_2$ to MBC-11 were used: (1:2), (1:1), (2:1) and higher (~12:1). To assess the degree of hydrolysis, the formation of arabinosylcytosine monophosphate (Ara-CMP) (in %) was recorded 24 hours later at 25° C.

The addition of $MgCl_2$ to the conjugate solutions resulted in a marked improvement in the stability of the conjugate. Several samples, mainly in water, showed an increase in Ara-CMP content of only 0.2% 8 hours later at 25° C., as compared to previous observations with an increase of ~2% (Table 1). In general, samples prepared in water were more stable than those prepared using buffer solutions. The exceptions were the samples with a large excess of $MgCl_2$, for which the stability of the conjugate in buffer solutions and water was relatively comparable.

TABLE 1

| | Effect of $MgCl_2$ on the formation of Ara-CMP at 25° C. | | | | | |
|---|---|---|---|---|---|---|
| Buffer Solution | $MgCl_2$ concentration (mmol/L) | Molar ratio of $MgCl_2$:MBC-11 | Content of Ara-CMP (%) | | | |
| | | | t* = 0 | t = 4 | t = 8 | t = 24 |
| Tartrate | — | — | 3.8 | 5.3 | 6.6 | 11.7 |
| | 0.87 | 1:2 | 2.5 | 3.5 | 4.5 | 8.4 |
| | 1.73 | 1:1 | 2.6 | 3.3 | 4.1 | 7.3 |
| | 3.5 | 2:1 | 2.5 | 3.0 | 3.5 | 5.5 |
| | 20 | ~12:1 | 2.6 | 2.7 | 3.0 | 3.8 |
| Succinate | — | — | 3.5 | 5.0 | 6.4 | 11.5 |
| | 0.87 | 1:2 | 2.6 | 3.5 | 4.4 | 7.9 |
| | 1.73 | 1:1 | 2.5 | 3.1 | 3.7 | 5.6 |
| | 3.5 | 2:1 | 2.6 | 3.1 | 3.7 | 5.8 |
| | 20 | ~12:1 | 2.5 | 2.7 | 2.9 | 3.6 |
| Water | 0.87 | 1:2 | 2.6 | 3.3 | 4.0 | 6.8 |
| | 1.73 | 1:1 | 2.5 | 2.8 | 3.2 | 4.6 |
| | 3.5 | 2:1 | 2.7 | 2.7 | 2.9 | 3.7 |
| | 20 | ~12:1 | 2.6 | 2.7 | 2.9 | 3.5 |

*t—time (hour)

According to the results of the experiment, a high hydrolytic stability of the conjugate is provided at a molar ratio of $MgCl_2$ to conjugate of 1:1. As shown in table, the use of water as a solvent and the molar ratio of $MgCl_2$ to MBC-11 of 2:1 provides for the highest stability of the conjugate in aqueous solutions. At higher $MgCl_2$ concentrations, there was a slight decrease in the effect, but the stability remained at a high level (FIG. 1).

The use of calcium chloride as a stabilizer against hydrolytic decomposition in both buffer solutions and water was also investigated; the hydrolysis rate constant was compared with the constant for $MgCl_2$. In water, at a molar ratio of $MgCl_2$ or $CaCl_2$ to MBC-11 of 2:1, the hydrolysis rate constants turned out to be similar (K=0.0005) and significantly exceeded the values for the aqueous solution of the trisodium salt of the etidronate-cytarabine conjugate not containing the above said salts (K=0, 0044). If molar ratios were less than 2:1, the hydrolysis rate was lower for solutions containing $MgCl_2$.

The addition of divalent metal salts to the aqueous solution of MBC-11 in a molar ratio of 2:1 leads to a slowdown in the hydrolysis reaction by 90%. Thus, the preferred ratio of the divalent metal salt to the etidronate-cytarabine conjugate shall be 2:1, but the positive effect of salts on the hydrolytic stability is manifested even at a ratio of 1:1 and is preserved at a ratio of more than 2:1 (at a ratio of 12:1 and higher).

Thermal Behavior of Solutions for Lyophilization

The thermal properties of the solutions provided for lyophilization were investigated. Differential Scanning calorimetry (DSC) was used to identify the lowest possible transient temperature in the solution throughout the entire lyophilization process, including freezing and dehydration. For the solutions of most pharmaceutical products, this parameter is represented by the glass transition temperature or "$T_{gt}$". All components and their amounts in the solution contribute to the final value of $T_{gt}$. This temperature is usually several degrees below the temperature at which the sintered material can crumble during the lyophilization process (collapse temperature, $T_c$). Without determining the collapse temperature by such methods as cryomicroscopy, the glass transition temperature can be used to select the primary drying temperature. Until the primary drying is completed, the initial drying temperature should be set in such a manner that there are no vials for which the glass transition temperature has been exceeded (or $T_c$, if known). Otherwise, the structure of the sintered material may get broken. On the one hand, the lyophilization temperature should be close to $T_{gt}$, so that the process proceeds efficiently, and on the other hand, it cannot exceed $T_{gt}$ due to process requirements and qualitative product parameters. Thus, the values of collapse and glass transition temperature are important parameters for calculating safe upper temperature limits, which can be used for lyophilization.

Based on the proposed filling of the vials with the drug (100 mg of active ingredient per vial), potential solutions for filling were prepared. The excipients included sterile water for injection (SWFI), 50 mM succinate and tartrate buffers at pH 5, $MgCl_2$, sulfobutylether β-cyclodextrin (SBEβCD), mannitol and dextran 40. In addition, for solutions containing mannitol, a study of the effect of the annealing stage (the lyophilization process stage when the samples are kept at a certain temperature below the freezing point for a certain period of time) on the improvement the crystallinity of the finished product was performed. The DSC results are shown in Table 2.

TABLE 2

Thermal behaviour of solutions for lyophilization

| Solvent | MBC-11 (mg/mL) | Excipient | pH | Thermal effect (event) |
|---|---|---|---|---|
| SWFI | 50 | — | 5.2 | −21° C. ($T_{gt}$) |
| | 100 | — | 5.4 | −21° C. ($T_{gt}$) |
| | 100 | $MgCl_2$, 173 mmol/L | — | −22° C. (endothermicity) |
| | 100 | $MgCl_2$, 350 mmol/L | — | −26° C. (endothermicity) |
| | 50 | 20% SBEβCD | — | −26° C. ($T_{gt}$) |
| | 50 | $MgCl_2$, 173 mmol/L | 4.23 | −26° C. (endothermicity) |
| | 50 | $MgCl_2$, 86.5 mmol/L | 4.52 | −34° C. ($T_{gt}$) −21° C. (endothermicity) |
| | 25 | $MgCl_2$, 86.5 mmol/L | 4.35 | −26° C. (endothermicity) |
| | 25 | $MgCl_2$, 43.25 mmol/L | 4.59 | −22° C. ($T_{gt}$) −21° C. (endotherm) |
| | 50 | $MgCl_2$, 173 mmol/L Mannitol, 25 mg/mL | — | $T_{gt}$/endothermicity before alloy expansion |
| | 50 | $MgCl_2$, 86.5 mmol/L Mannitol, 25 mg/mL | — | $T_{gt}$/endothermicity before alloy expansion |
| | 25 | $MgCl_2$, 86.5 mmol/L Mannitol, 25 mg/mL | — | $T_{gt}$/endothermicity before alloy expansion |
| | 25 | $MgCl_2$, 43.25 mmol/L Mannitol, 25 mg/mL | — | Possible crystallization at −27° C. |
| | 25 | $MgCl_2$, 43.25 mmol/L Mannitol, 25 mg/mL Annealing at −20° C. | — | None crystallization after temperature processing, specific endothermicity at −22° C. |
| | 25 | $MgCl_2$, 43.25 mmol/L Mannitol, 25 mg/mL Annealing at −24° C. | — | None crystallization after annealing was observed, weak endothermicity at −22° C. |
| | 100 | $MgCl_2$, 173 mmol/L Dextran-40 5% | — | −29° C. ($T_{gt}$) |
| | 50 | $MgCl_2$, 173 mmol/L Dextran-40 5% | — | −36° C. ($T_{gt}$) |
| | 50 | $MgCl_2$, 86.5 mmol/L Dextran-40 5% | — | −24° C. ($T_gt$) |
| | 25 | $MgCl_2$, 86.5 mmol/L Dextran-40 5% | — | −27° C. ($T_{gt}$) |
| | 25 | $MgCl_2$, 43.25 mmol/L Dextran-40 5% | — | −21° C. ($T_{gt}$) |
| Tartrate buffer | 25 | $MgCl_2$, 86.5 mmol/L | 4.48 | −40° C. ($T_{gt}$) −30° C. (crystallization) −22° C. (endothermicity) |
| | 25 | $MgCl_2$, 86.5 mmol/L Mannitol, 25 mg/mL | — | −40° C. ($T_{gt}$) |
| | 25 | $MgCl_2$, 86.5 mmol/L Dextran-40 5% | — | −26° C. ($T_{gt}$) |
| Succinate buffer | 25 | $MgCl_2$, 86.5 mmol/L | 4.52 | −34° C. (crystallization) −26° C. (endothermicity) |
| | 25 | $MgCl_2$, 86.5 mmol/L Mannitol, 25 mg/mL | — | $T_{gt}$/endothermicity before alloy expansion |
| | 25 | $MgCl_2$, 86.5 mmol/L Dextran-40 5% | — | −30° C. ($T_{gt}$) |

The development of endothermicity, later defined as enthalpy relaxation, was typical of most samples containing $MgCl_2$.

Investigation of Chemical Stability of Solutions for Lyophilization

Several solutions for lyophilization were studied in a short-term study of chemical stability at 25° C., given that buffer solutions were not used. The study results are shown in Table 3.

TABLE 3

Chemical stability of solutions for lyophilization

| Ser. No. | MBC-11 (mg/mL) | Excipient | Purity of the main peak according to HPLC in % | | | | Hydrolysis constant (K) |
|---|---|---|---|---|---|---|---|
| | | | *t = 0 | t = 3 | t = 6 | t = 24 | |
| 1 | 100 | — | 91.30 | 90.79 | 89.70 | 84.62 | 0.0032 |
| 2 | 100 | MgCl$_2$, 173 mmol/L (1 × salt) | 91.33 | 91.16 | 90.76 | 86.87 | 0.0022 |
| 3 | 100 | MgCl$_2$, 173 mmol/L + Dextran 5% | 91.37 | 91.27 | 90.73 | 87.84 | 0.0017 |
| 4 | 50 | — | 91.38 | 90.38 | 89.53 | 84.11 | 0.0034 |
| 5 | 50 | MgCl$_2$, 173 mmol/L (2 × salt) | 91.4 | . | 90.9 | 90.24 | 0.0005 |
| 6 | 50 | MgCl$_2$, 173 mmol/L (2 × salt) + mannitol, 25 mg/mL | 91.39 | 91.23 | 91.09 | 90.46 | 0.0004 |
| 7 | 50 | 20% SBEβCD | 91.27 | 90.65 | 89.75 | 85.40 | 0.0028 |
| 8 | 50 | MgCl$_2$, 86.5 mmol/L(1 × salt) + Dextran 5% | 91.16 | 90.86 | 90.81 | 89.67 | 0.0007 |
| 9 | 25 | MgCl$_2$, 86.5 mmol/L (2 × salt) + Dextran 5% | 91.11 | 90.93 | 90.87 | 90.16 | 0.0004 |
| 10 | 25 | MgCl$_2$, 43.3 mmol/L(1 × salt) + Dextran 5% | 91.28 | 90.94 | 90.67 | 89.80 | 0.0006 |
| 11 | 25 | Mannitol, 25 mg/mL | 91.24 | 90.16 | 89.35 | 83.71 | 0.0036 |

*t—time (hour)

As mentioned earlier, the most stable solutions contain MgCl$_2$ in a molar ratio to the drug substance of 2:1. Samples with a 1:1 ratio are less stable, but still exhibit low values of the hydrolysis constant. It has been found that the presence of mannitol or dextran, contrary to expectations, does not lead to an improvement in chemical stability. In solutions with a concentration of 100 mg/mL, signs of sedimentation were found on the following day, which could affect the purity values listed in the table. The samples given in bold showed sufficient stability to be prospective solutions to be filled into vials for lyophilization. Within 24 hours at 25° C., the content of the etidronate-cytarabine conjugate in these samples decreased by 1-1.5% only.

Alternative Lyophilized Dosage Forms

Several solutions to be filled into the vials have been selected as options for the preparation of the lyophilized dosage form. The dosage forms selected are shown below (Table 4).

TABLE 4

Dosage forms selected

| | MBC-11 (mg/mL) | Excipient, (in SWFI, pH 5) | Hydrolysis rate constant (K) | Thermal characteristic (° C.) | |
|---|---|---|---|---|---|
| A | 50 | MgCl$_2$ (2 × salt) 173 mmol/L | 0.0005 | −26 | Endotherm |
| B | 50 | MgCl$_2$ (2 × salt) mmol/L + mannitol 25 mg/mL | 0.0004 | — | — |
| C | 50 | 20% SBEβCD | 0.0028 | −26 | $T_{gt}$ |
| D | 50 | MgCl$_2$ (1 × salt) 86.5 mmol/L + Dextran 5% | 0.0007 | −24 | $T_{gt}$ |
| E | 25 | MgCl$_2$ (2 × salt) 86.5 mmol/L + Dextran 5% | 0.0004 | −27 | $T_{gt}$ |
| F | 25 | MgCl$_2$ (1 × salt) 43.3 mmol/L + Dextran 5% | 0.0006 | −21 | $T_{gt}$ |

These solutions were lyophilized using a conventional cycle with a primary temperature of the drying shelf set at −26° C. and a secondary drying temperature of 32° C. The annealing stage was not used (Table 5).

solution. As a result of the lyophilization cycle, a sintered material with no cracks was formed.

The lyophilized material was kept at 40° C. to determine stability. Hydrolysis was evaluated by the formation of

TABLE 5

Characteristics of the sintered material

| Form | MBC-11 (mg/mL) | Excipient, in SWFI with pH 5 | Appearance* | Dissolution | Purity before lyophilization (%) | Purity after lyophilization (%) |
|---|---|---|---|---|---|---|
| A | 50 | MgCl$_2$ (2 × salt) 173 mmol/L | 4 | 10 sec | 95.8 | 95.5 |
| B | 50 | MgCl$_2$ (2 × salt) mmol/L + mannitol 25 mg/mL | 5 | 10 sec | 95.9 | 95.7 |
| C | 50 | 20% SBEβCD | 2 | 10 sec | 95.5 | 95.5 |
| D | 50 | MgCl$_2$ (1 × salt) 86.5 mmol/L + Dextran 5% | 3 | 1 min | 95.7 | 95.7 |
| E | 25 | MgCl$_2$ (2 × salt) 86.5 mmol/L + Dextran 5% | 4 | 1 min | 95.8 | 95.8 |
| F | 25 | MgCl$_2$ (1 × salt) 43.3 mmol/L + Dextran 5% | 4 | 1 min | 95.9 | 95.5 |

*Explanation of the appearance characteristics: 1—excellent; 2—cracked; 3—slightly reduced in volume; 4—decrease in volume/fusion; 5—complete collapse/deformation.

Medicinal forms A, C, D and E were selected for short-term accelerated stability studies at 40 and 60° C. To assess the degree of hydrolysis, the formation of Ara-CMP (in %) was evaluated. All dosage forms containing MgCl$_2$ showed similar increases in Ara-CMP content of approximately 0.4-0.5% at 40° C. 21 days after. For the samples with a molar ratio of 2:1, the formation of Ara-CMP was somewhat less than that of the samples with a molar ratio of 1:1. Eight days later, at 60° C., the Ara-CMP content increased by approximately 0.8%. The SBEβCD sample showed a larger increase in the Ara-CMP content 8 days later (0.6% at 40° C. and 1.6% at 60° C.). Approximate shelf life estimates obtained by the Arrhenius equation show that prolonged storage at 2-8° C. should ensure a shelf life of at least two years, given that the Ara-CMP level indicated in the specification should be less than 5.0%.

Investigation of the Effect of Using the Annealing Stage

To evaluate the use of the annealing stage, a dosage form with a molar ratio of MgCl$_2$ to MBC-11 (2:1) was selected as a part of the cycle. Annealing is the stage of the process, during which the samples are kept at a specific temperature below the freezing point for a certain period of time. It is used to facilitate the crystallization of active ingredients and fillers, as well as to change the shape and size of ice crystals due to Oswald ripening. Annealing can affect both the cycle time and the stability of the finished product.

The modulated DSC used to characterize the dosage form with the active substance at a concentration of 50 mg/mL showed a clear crystallization at −37° C., which had not previously been isolated from the enthalpic component (−27° C.) during rapid SWFItch to the specified temperature conditions. The observation also confirmed for what reason the fusion occurred in the sintered material during the first lyophilization cycle at the ultimate drying temperature of −26° C. The annealing phase at −35° C., which is two degrees higher than the glass transition temperature, was added into the lyophilization cycle. For lyophilization, 5 mL vials were used, each of which was filled with 2 mL of Ara-CMP. 21 days (3 weeks) after, the Ara-CMP content increased by 0.4%, which was similar to the sample obtained using the lyophilization cycle without the annealing stage.

Despite the fact that the annealing step does not have clear advantages or disadvantages in relation to chemical stability, it is recommended to use it for obtaining larger and more homogeneous crystals, thereby increasing the efficiency of the cycle.

Stability of the Proposed Solutions to be Filled into Vials for Lyophilization

Several studies of the stability of the proposed solutions to be filled into the vials for lyophilization were performed. During the first study, the following solutions were evaluated at 2-8° C., 25° C. and ambient temperature for 30 hours (Table 6). The amount of MBC-11 was 100 mg per bottle.

TABLE 6

Proposed solutions to be filled into

| Formulation composition | MBC-11 (mg/mL) | Volume of solution to be filled into (ml) |
|---|---|---|
| MgCl$_2$:MBC-11 (2:1) | 50 | 2 |
| MgCl$_2$:MBC-11 (1:1) and Dextran-40 5% | 50 | 2 |
| MgCl$_2$:MBC-11 (2:1) and Dextran-40 5% | 25 | 4 |
| MgCl$_2$:MBC-11 (2:1) and Dextran-40 10% | 25 | 4 |

All solutions with a MgCl$_2$:MBC-11 molar ratio of 2:1 showed in general identical levels of MBC-11 degradation (an increase in Ara-CMP content of 0.75% within 30 hours at ambient temperature). At the same time, the content of Ara-CMP in a solution with a ratio of 1:1 in most cases was approximately 0.1-0.3% higher. This result is consistent with other observations, attesting to the fact that when the ratio of stabilizer to conjugate is increased from 1:1 and more, the hydrolytic stability of the solutions increases. The amount of MBC-11 or the amount of dextran present does not have a significant effect on chemical stability.

Investigation of Physical Stability of Solutions to be Filled into

As mentioned earlier, the use of divalent cations leads to physical instability, namely, an insoluble precipitate can be formed as a result of the use of divalent cations. Studies were therefore conducted to evaluate the physical stability of solutions containing different concentrations of etidronate-cytarabine conjugate (10 mg/mL to 50 mg/mL) with $MgCl_2$ to drug ratio of 1:1 to 10:1. The solutions prepared were stored in glass bottles, some of them were filtered through a 0.2 μm polyvinylidene fluoride (PVDF) membrane. The study was performed at 2-8° C. and room temperature.

A decrease in the total concentration of MBC-11 in a solution for filling vials for lyophilization in general improved the physical stability of solutions obtained by dissolving the lyophilizate. All solutions with a concentration of 10 mg/mL under both conditions (i.e., at 2-8° C. and room temperature) were physically stable for 27 hours. 27 hours later, some precipitation showed in one of the samples stored at 2-8° C. Solutions with a concentration of 25 mg/mL were stable for 24 hours. After 24 hours, several dosage forms showed signs of precipitation. In solutions with a concentration of 25 mg/mL, a precipitate was observed at 2-8° C. 8 hours after. Also, the chemical stability was monitored during the study, and the data obtained corresponded to the results of previous studies. The summary tables of physical observations are presented below. Code of visual observation results:
* transparent solution (no solid particles),
** small flakes,
*** large white flakes.

TABLE 7

Results of visual observations of solutions for filling at 2-8° C.

| Dosage form code | Formulation composition | t = 0 | t = 2 | t = 4 | t = 8 | t = 24 | t = 27 | t = 30 | t = 48 |
|---|---|---|---|---|---|---|---|---|---|
| F1a-NF | 50 mg/mL MBC-11 trisodium salt and 173 mmol/L $MgCl_2$ (no filtration after preparation) | * | * | * | ** | *** | *** | *** | *** |
| F1a-F | 50 mg/mL MBC-11 trisodium salt and 173 mmol/L $MgCl_2$ (filtered after preparation) | * | * | * | * | *** | *** | *** | *** |
| F2a-NF | 50 mg/mL MBC-11 trisodium salt and 86.5 mmol/L $MgCl_2$ (no filtration after preparation) | * | * | * | * | *** | *** | *** | *** |
| F2a-F | 50 mg/mL MBC-11 trisodium salt and 86.5 mmol/L $MgCl_2$ (filtered after preparation) | * | * | * | * | * | *** | *** | *** |
| F1b-NF | 25 mg/mL MBC-11 trisodium salt and 173 mmol/L $MgCl_2$ (no filtration after preparation) | * | * | * | * | * | * | * | ** |
| F1b-F | 25 mg/mL MBC-11 trisodium salt and 173 mmol/L $MgCl_2$ (filtered after preparation) | * | * | * | * | * | * | * | ** |
| F2b-NF | 25 mg/mL MBC-11 trisodium salt and 86.5 mmol/L $MgCl_2$ (no filtration after preparation) | * | * | * | * | * | ** | ** | ** |
| F2b-F | 25 mg/mL MBC-11 trisodium salt and 86.5 mmol/L $MgCl_2$ (filtered after preparation) | * | * | * | * | * | * | * | ** |
| F1c-NF | 10 mg/mL MBC-11 trisodium salt and 173 mmol/L $MgCl_2$ (no filtration after preparation) | * | * | * | * | * | * | * | * |
| F1c-F | 10 mg/mL MBC-11 trisodium salt and 173 mmol/L $MgCl_2$ (filtered after preparation) | * | * | * | * | * | * | * | * |
| F2c-NF | 10 mg/mL MBC-11 trisodium salt and 86.5 mmol/L $MgCl_2$ (no filtration after preparation) | * | * | * | * | * | * | * | ** |
| F2c-F | 10 mg/mL MBC-11 trisodium salt and 86.5 mmol/L $MgCl_2$ (filtered after preparation) | * | * | * | * | * | * | * | * |

TABLE 8

Results of visual observations of solutions for filling at room temperature.

| Dosage form code | Formulation composition | t = 0 | t = 2 | t = 4 | t = 8 | t = 24 | t = 27 | t = 30 | t = 48 |
|---|---|---|---|---|---|---|---|---|---|
| F1a-NF | 50 mg/mL MBC-11 trisodium salt and 173 mmol/L MgCl$_2$ (no filtration after preparation) | * | * | * | * | *** | *** | *** | *** |
| F1a-F | 50 mg/mL MBC-11 trisodium salt and 173 mmol/L MgCl$_2$ (filtered after preparation) | * | * | * | * | *** | *** | *** | *** |
| F2a-NF | 50 mg/mL MBC-11 trisodium salt and 86.5 mmol/L MgCl$_2$ (no filtration after preparation) | * | * | * | * | *** | *** | *** | *** |
| F2a-F | 50 mg/mL MBC-11 trisodium salt and 86.5 mmol/L MgCl$_2$ (filtered after preparation) | * | * | * | * | *** | *** | *** | *** |
| F1b-NF | 25 mg/mL MBC-11 trisodium salt and 173 mmol/L MgCl$_2$ (no filtration after preparation) | * | * | * | * | * | ** | ** | ** |
| F1b-F | 25 mg/mL MBC-11 trisodium salt and 173 mmol/L MgCl$_2$ (filtered after preparation) | * | * | * | * | * | ** | ** | ** |
| F2b-NF | 25 mg/mL MBC-11 trisodium salt and 86.5 mmol/L MgCl$_2$ (no filtration after preparation) | * | * | * | * | * | ** | ** | ** |
| F2b-F | 25 mg/mL MBC-11 trisodium salt and 86.5 mmol/L MgCl$_2$ (filtered after preparation) | * | * | * | * | * | * | * | ** |
| F1c-NF | 10 mg/mL MBC-11 trisodium salt and 173 mmol/L MgCl$_2$ (no filtration after preparation) | * | * | * | * | * | * | * | * |
| F1c-F | 10 mg/mL MBC-11 trisodium salt and 173 mmol/L MgCl$_2$ (filtered after preparation) | * | * | * | * | * | * | * | * |
| F2c-NF | 10 mg/mL MBC-11 trisodium salt and 86.5 mmol/L MgCl$_2$ (no filtration after preparation) | * | * | * | * | * | * | * | * |
| F2c-F | 10 mg/mL MBC-11 trisodium salt and 86.5 mmol/L MgCl$_2$ (filtered after preparation) | * | * | * | * | * | * | * | * |

Thus, as a result of the studies performed, it was found that when the ratio of stabilizer to conjugate increases from 1:1, the physical stability of the solutions increases. In addition, it was found that an increase in the concentration of the etidronate-cytarabine conjugate in a solution in more than 25 mg/mL affects its physical stability adversely.

Investigation of Compatibility with the Medium for Intravenous Administration

A solution with a concentration of 25 mg/mL MBC-11 and a molar ratio of MgCl$_2$ to MBC-11 of 2:1 with dextran 5% was prepared and then diluted to a concentration of 1 mg/mL in different media for intravenous administration: phosphate buffered saline, natural saline solution, Dulbecco's phosphate buffered saline, isotonic sodium chloride solution, Lactated Ringers Solution, and dextrose 5% in water (D5W) solution. Dextrose solution D5W showed the lowest degradation of MBC-11; the Ara-CMP content increased by 1% within one day. This increase was similar to an aqueous control sample, indicating that dextrose does not adversely affect the active pharmaceutical ingredient MBC-11.

Investigation of Physical and Hydrolytic Stability of Reconstituted Lyophilizates The next study used one of two selected variants of the dosage form. The selected variant has the composition shown in Table 9.

TABLE 9

Composition of the vial.

| Variant of the dosage form | Filling volume | Amount of MBC-11 in the form of trisodium salt (mg) | Amount of MBC-11 in form the of trisodium salt (μmol) in 1 vial | Amount of MgCl$_2$ (mg) | Amount of MgCl$_2$ (μmol) |
|---|---|---|---|---|---|
| 2 | 5 mL | 100 | 173 | 32.9 | 346 |

The lyophilized dosage form was evaluated for compatibility with three different media for intravenous administration within 24 hours: sterile water for injection (SWFI), D5W and 0.9% sodium chloride solution. Low and high infusion doses for clinical use were investigated, they amounted to 0.25 mg/mL and 10 mg/mL MBC-11 in the solution, respectively. The lyophilized dosage form was first dissolved in 5 mL SWFI to the MBC-11 trisodium salt concentration of 20 mg/mL, and then it was placed in glass vials and diluted with each medium for intravenous administration until the infusion doses under study were obtained. The solutions thus obtained were kept at 2-8° C. and 25° C. for 24 hours, and the evaluation of the samples in appearance, content and purity at the points t=0, 2, 4, 6 and 24 hours was performed.

At each control point, solutions for intravenous administration with a high dosage were evaluated in appearance, after which they were diluted to a nominal analytical concentration of 1 mg/mL with a solvent used in the analytical method for evaluating the substance purity. The samples thus obtained were used to determine the purity and content of the active pharmaceutical ingredient.

The results showed that samples with a low concentration were physically stable within 24 hours. Samples containing a high dose were physically stable up to 6 hours. Based on the data obtained in 6 hours, the best chemical stability was achieved when D5W or water was used. For all dosage form solutions prepared, the maximum increase in Ara-CMP was 1.4% in low-dose sodium chloride-based intravenous media stored at 25° C. for 6 hours. For comparison, a sample with a low dose of MBC-11 in D5W showed only a 0.5% increase in the Ara-CMP content under the same conditions.

Example of Preparation of the Stable Dosage Form

We weigh 14.1±0.1 g magnesium chloride hexahydrate in the clean 1 L bottle. Add 985.9±1.0 g sterile water for injection to the same bottle. Mix the resulting mixture with a magnetic stirrer at room temperature until completely dissolved.

Weigh 15.69±0.05 g MBC-11 trisodium salt (corrected for water content only) in 1 L bottle. Further, add 744.1±3.0 g the magnesium chloride solution, prepared above, to the same bottle. Mix the resulting mixture at room temperature until completely dissolved. Take a 3 mL aliquot to monitor the pH. Filter the resulting solution aseptically through a 0.2 μm polyvinylidene fluoride (PVDF) membrane into a sterile container using a Millipore SCGVU11RE filter apparatus. Pour the resulting filtrate into 20 mL glass bottles, 5.4 mL of the filtrate into each glass bottle, and lyophilize them.

Vials with the finished product, partially sealed with a rubber stopper, are completely sealed by hold-down plates of the freezer chamber and pressurized with aluminum and plastic caps, and then placed into a cooler for storage at 2-80° C.

For intravenous administration, a reconstituted lyophilizate solution is prepared by preferably dissolving the contents of the vial in water or 5DW so that the drug concentration is not more than 10 mg/mL. It was found that the reconstituted drug solution does not have physical stability at high concentrations. The reconstituted solution thus obtained is transferred to an standard volume infusion bag containing natural saline solution or 5DW. The number of vials with reconstituted lyophilizate solution per infusion bag is determined according to the dosage prescribed by the doctor.

Various embodiments of the invention relate to the use of a stable dosage form of the etidronate-cytarabine conjugate of the invention for the treatment of primary bone cancer or bone lesion caused by a malignant neoplasm.

The embodiments of the invention are also provided by method of treatment of bone lesions caused by malignant neoplasms. The method involves the administration of this stable form of the etidronate-cytarabine conjugate, or a pharmaceutically acceptable salt thereof, prepared by the method described, at an effective dose to the patient. In various embodiments, the dosage form can be administered parenterally, for example, by intravenous infusion. In various embodiments, oncology diseases can include multiple myeloma, osteosarcoma, bone metastases caused by breast, prostate or thyroid cancer. In various embodiments of the present invention, the stable dosage form of the etidronate-cytarabine conjugate can be administered to patients in combination with other drugs in different treatment regimens.

The present invention also relates to a kit comprising a lyophilized dosage form of the etidronate-cytarabine conjugate in a container, an aqueous solution or a dextrose 5% solution, inline filters. The dosage form is suitable for parenteral administration of effective doses of the conjugate, as well as for infusion administration, i.e. for aseptic connection with intravenous valves, tubes, parts, lines, etc., or for transportation of the drug between infusion devices.

The kit may also include one or more dosage forms packed together with instruction materials relating to the administration of the dosage form or with instruction materials including labeling instrumentation, for example labels, tags, CDs, DVDs, recorded cassettes, etc. describing the use of the drug form in a manner approved by the government regulatory body.

Thus, the dosage form in the present invention provides one or more unit drug doses, adapted to the practice of the method of administration, which comprise an etidronate-cytarabine conjugate, or a pharmaceutically acceptable salt thereof, at a suitable concentration in a biocompatible carrier packaged to maintain sterility and to protect the active ingredient from degradation.

Despite the fact that the invention has been described with reference to the disclosed embodiments, it should be apparent to those skilled in the art that the specific, detailed experiments described are for the purpose of illustrating the present invention only, and should not be construed as in any way limiting the scope of the invention. It should be understood that various modifications are possible without deviation from the chief matter of the present invention.

The invention claimed is:

1. A lyophilizate stable dosage form suitable for a solution for parenteral administration comprising an etidronate-cytarabine conjugate, or a pharmaceutically acceptable salt thereof, and a stabilizer, which is a divalent metal salt, with a molar ratio of stabilizer to etidronate-cytarabine conjugate, or pharmaceutically acceptable salt thereof, of 1:1 to 12:1.

2. The lyophilizate stable dosage form as claimed in claim 1, wherein the pharmaceutically acceptable salt of the etidronate-cytarabine conjugate is the trisodium salt of the etidronate-cytarabine conjugate.

3. The lyophilizate stable dosage form as claimed in claim 1, wherein magnesium or calcium salts are used as the divalent metal salt.

4. The lyophilizate stable dosage form as claimed in claim 1, wherein calcium chloride or magnesium chloride is used as the divalent metal salt.

5. The lyophilizate stable dosage form as claimed in claim 1, wherein the molar ratio of stabilizer to etidronate-cytarabine conjugate, or a pharmaceutically acceptable salt thereof, is from 1:1 to 2:1.

6. The lyophilizate stable dosage form as claimed in claim 1, wherein the molar ratio of stabilizer to etidronate-cytarabine conjugate, or a pharmaceutically acceptable salt thereof, is 2:1.

7. A method for the preparation of a stable dosage form as claimed in claim 1 includes the following:
 prepare an aqueous solution containing an etidronate-cytarabine conjugate, or a pharmaceutically acceptable salt thereof, and a stabilizer which is a divalent metal salt, with the selected molar ratio of stabilizer to conjugate from 1:1 to 12:1;
 perform sterile filtration of the solution produced;
 dispense the solution produced to containers for lyophilization;
 perform lyophilization.

8. The method as claimed in claim 7, wherein the molar ratio of stabilizer to conjugate is from 1:1 to 2:1.

9. The method as claimed in claim 7, wherein the molar ratio of stabilizer to conjugate is 2:1.

10. The method as claimed in claim 7, wherein the concentration of the etidronate-cytarabine conjugate, or a pharmaceutically acceptable salt thereof, in the aqueous solution is ≤25 mg/mL.

11. The method as claimed in claim 7, wherein 20 mL vials are used as containers.

12. The method as claimed in claim 7, wherein the sterile filtration of the solution produced is performed through a 0.2 μm sterile filter.

13. The parenteral solution obtained by dissolving the lyophilizate stable dosage form according as claimed in claim 1 in a pharmaceutically acceptable solvent suitable for parenteral administration.

14. The solution as claimed in claim 13, wherein the concentration of the lyophilizate stable dosage form in a pharmaceutically acceptable solvent is ≤10 mg/mL.

15. The solution as claimed in claim 13, wherein the pharmaceutically acceptable solvent is represented by sterile water for injection or dextrose 5% in water solution.

16. A method for the treatment of primary bone cancer or bone lesion caused by a malignant neoplasm, the method comprising administering the parental solution as claimed in claim 13 to a patient in need of treatment of a primary bone cancer or a bone lesion caused by a malignant neoplasm.

17. The method as claimed in claim 16, wherein the bone lesion is a multiple myeloma, bone metastases caused by breast, prostate or thyroid cancer, or metastatic lesions of other tissues and organs.

18. The method as claimed in claim 16, wherein the primary bone cancer is represented by osteosarcoma, Ewing's sarcoma, chondrosarcoma, fibrosarcoma.

* * * * *